United States Patent [19]

Leveen et al.

[11] 4,446,867
[45] May 8, 1984

[54] FLUID-DRIVEN BALLOON CATHETER FOR INTIMA FRACTURE

[76] Inventors: Robert F. Leveen, 312 Lombard St., Philadelphia, Pa. 19147; Eric G. Leveen, 85-27 Hearth Dr. - #3 Condo, Houston, Tex. 77054

[21] Appl. No.: 336,085

[22] Filed: Dec. 31, 1981

[51] Int. Cl.³ ............................................. A61M 29/02
[52] U.S. Cl. ............................. 128/344; 128/DIG. 12; 604/96; 604/97
[58] Field of Search ................ 128/DIG. 12, DIG. 13, 128/1 D, 325, 344, 207.15; 417/383, 384, 394; 604/18, 96, 97, 98, 99, 100, 101, 102, 123, 124, 207

[56] References Cited

U.S. PATENT DOCUMENTS

| | | |
|---|---|---|
| 2,826,193 | 3/1958 | Vineberg . |
| 3,467,101 | 9/1969 | Fogarty et al. . |
| 3,478,737 | 11/1969 | Rassman . |
| 3,513,836 | 5/1970 | Sausse . |
| 3,565,062 | 2/1971 | Kuris . |
| 3,769,960 | 11/1973 | Robinson ............................. 128/1 D |
| 4,154,227 | 5/1979 | Krause et al. . |
| 4,159,722 | 7/1979 | Walker . |
| 4,205,683 | 6/1980 | O'Neill .................................. 604/99 |
| 4,217,993 | 8/1980 | Jess et al. ..................... 128/DIG. 13 |
| 4,284,073 | 8/1981 | Krause et al. ....................... 128/1 D |
| 4,307,772 | 12/1981 | Evans . |

FOREIGN PATENT DOCUMENTS 2230283 1/1974 Fed. Rep. of Germany .
2460679 7/1979 France .

Primary Examiner—Kyle L. Howell
Assistant Examiner—Christine A. Fukushima
Attorney, Agent, or Firm—Gipple & Hale

[57] ABSTRACT

A novel balloon catheter apparatus for treatment of atherosclerotic occlusions within the cardiovascular system, comprising a catheter defining a through-going lumen, a fluid supply syringe attached to one end of the catheter for supplying fluid through the lumen, and a balloon attached to the other end of the catheter which is inflatable by forcing fluid through the lumen. A pulse generator is also attached to the catheter for generating pressure pulses in the fluid through the lumen, which pulses cause the balloon to sharply expand and contract at intervals. The pulse generator includes a pulse syringe communicating with the lumen, a spring-driven ram to contact the piston of the pulse syringe, and a cam rotor to move the ram away from the piston, thereby compressing the spring unitl the cam rotates further and the ram is released to strike the piston. When the balloon catheter is inserted in the cardiovascular system of the patient and guided to the occlusive site, the balloon is first inflated by the supply syringe until the balloon contacts the occlusive material, and then one or more pulses may be applied by the pulse generator through the fluid to rapidly expand and contract the balloon. Since the occlusive material is much more brittle than the surrounding wall, the wall expands in response to the pressure pulses while the occlusive material cracks and separates from the wall to be removed through normal cardiovascular processes.

11 Claims, 5 Drawing Figures

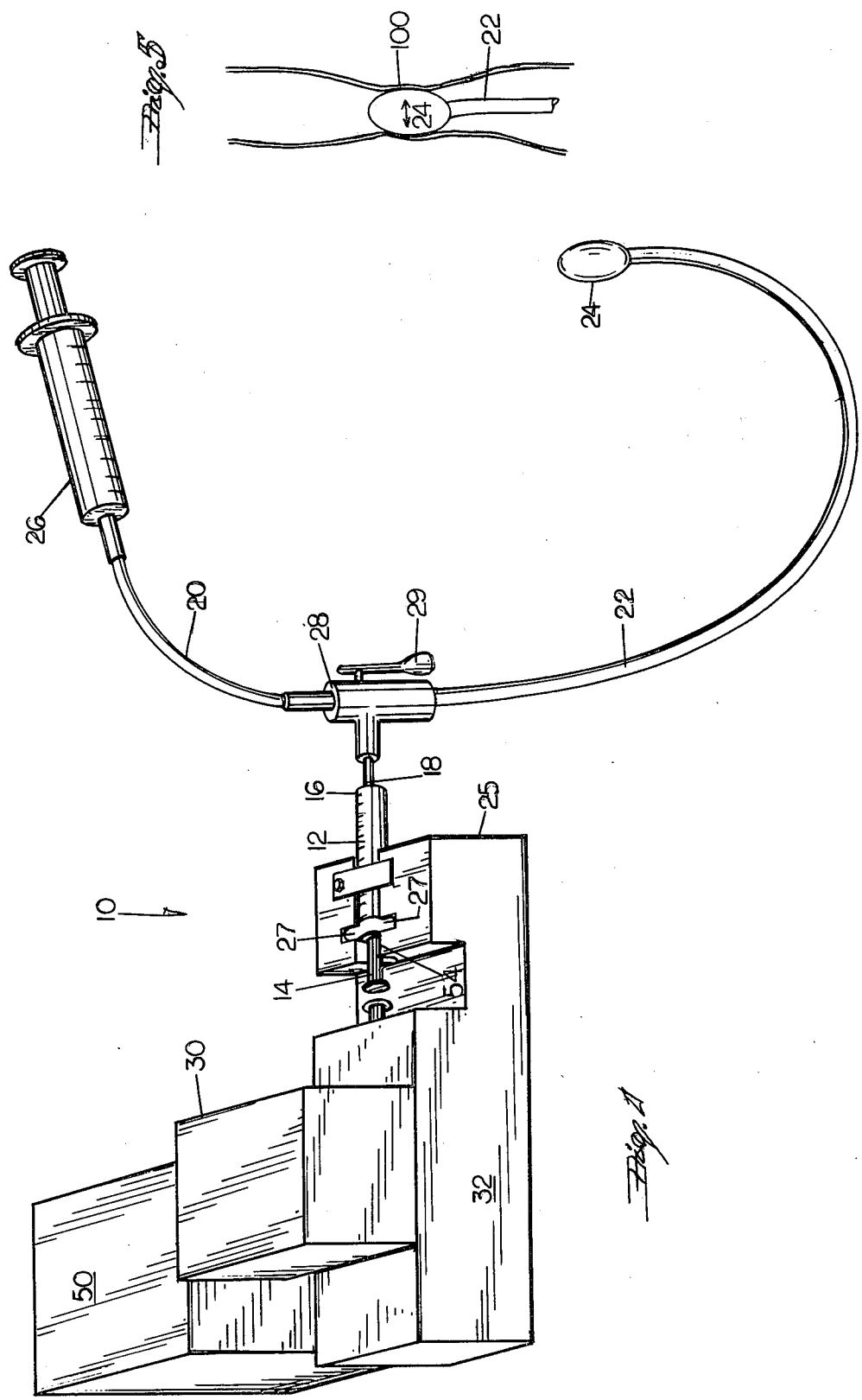

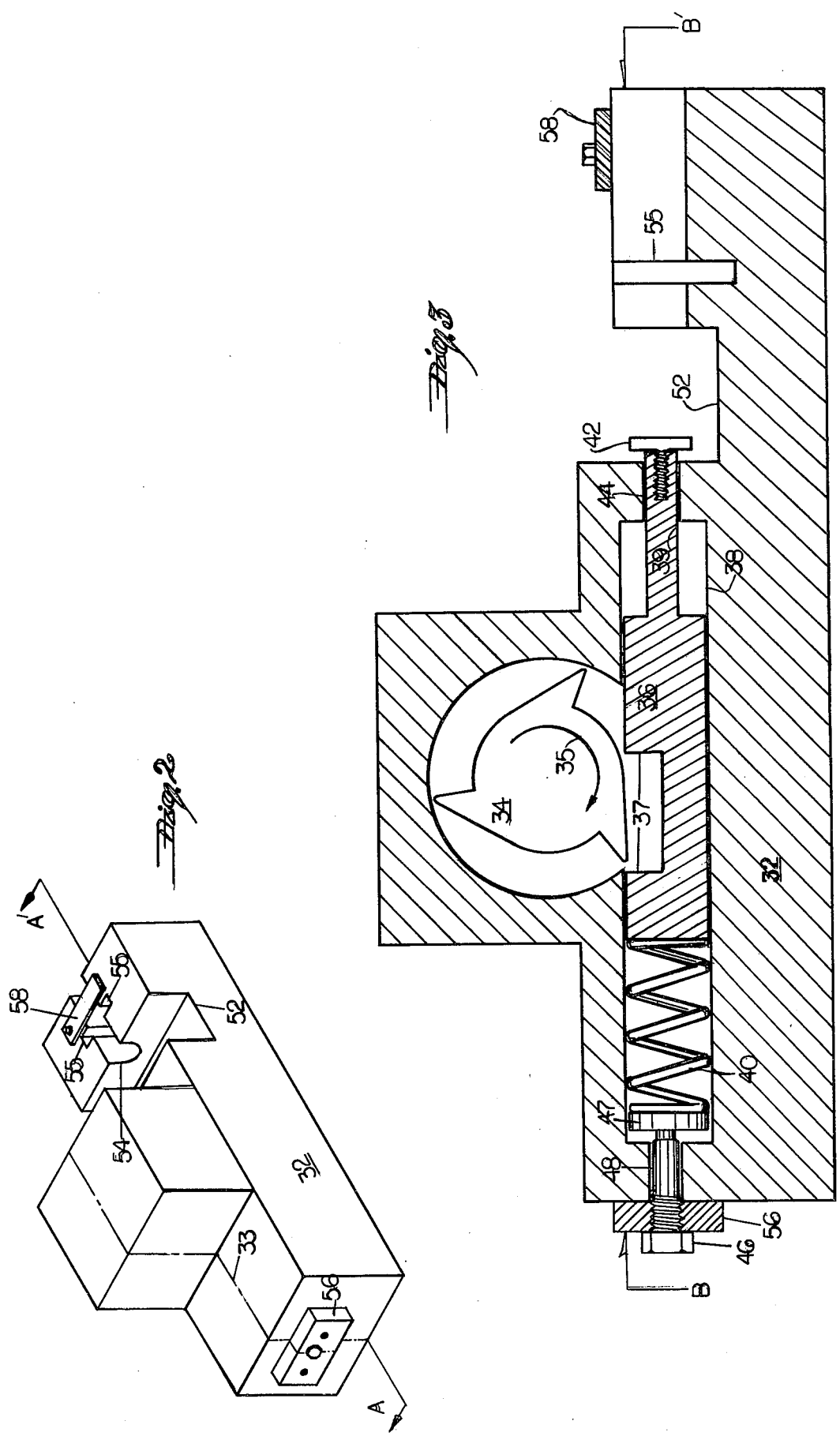

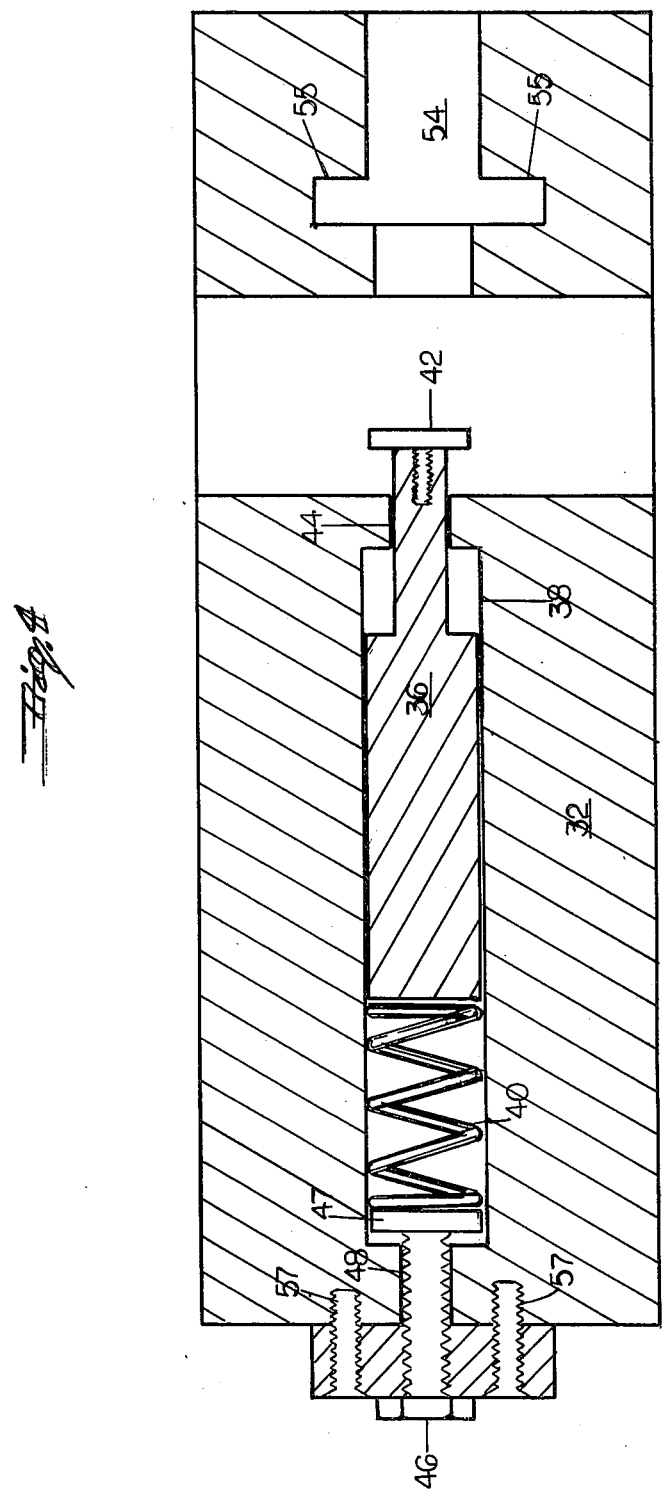

FLUID-DRIVEN BALLOON CATHETER FOR INTIMA FRACTURE

BACKGROUND OF THE INVENTION

This invention relates generally to medical instruments and procedures, and more specifically to a treatment process and apparatus for the disease known as atherosclerosis.

Of the various forms of arteriosclerosis, in which the internal passageway of an artery becomes restricted or blocked, the most common and important is known as atherosclerosis. This disease is characterized by intimal thickening resulting from an accumulation of lipids. These localized accumulations tend to occur in coronary, cerebral, and peripheral arteries, and complications of the disease are the major causes of death in this country. One-third of deaths reported are classified as caused by arteriosclerotic and degenerative heart disease, and the third most common cause after heart disease and cancer is cerebral vascular disease.

A number of reconstructive surgical procedures have been developed to relieve the occlusion resulting from atherosclerosis. These include resection with graft replacement, thrombo-endarectomy, and by-pass graft. However, these procedures necessarily involve a number of disadvantages. Many depend on removing an artery or vein from one part of the body for use in replacement of the occluded artery. Finding such an artery or vein which is both in a reasonably healthy condition and available for removal without replacement itself can be difficult. In a significant number of cases, arterial surgery cannot be conducted due to a condition commonly known as poor run-off, which refers to a lack of blood supply to the reconstruction site as a result of occlusion of arteries remote from the site.

Several procedures and apparatus have, therefore, been developed in the past several years to reduce or eliminate the need for by-pass or replacement surgery by re-establishing a lumen of proper diameter within the occluded artery. One such procedure is known as translumenal angioplasty in which a balloon catheter with a a sausage-shaped balloon of high tensile strength and low elasticity is inserted to the point of occlusion. The balloon tip is positioned within the remaining restricted lumen surrounded by the occlusive material. The balloon, when inflated to a pressure such as four atmospheres, becomes sufficiently rigid to dilate the intima and re-establish a full lumen. There are a significant number of occlusions which cannot be dilated in this fashion because the intima has achieved sufficient rigidity to resist the dilating pressure exerted by the balloon.

U.S. Pat. No. 3,886,943 discloses a surgical knife for removal of occlusive material from the intima of an arterial wall. The curved knife blade is mounted on a long rod with a handle for manipulation of the blade by the physician. Since the blade is necessarily of a fixed diameter, it cannot be used effectively in arteries smaller than the diameter, which requires the physician to retain on hand a number of blade of different diameters. Furthermore, the invention requires surgery to reach the approximate site of occlusion, since the blade rod is of limited length and is rigid.

U.S. Pat. No. 4,058,126 discloses a spring-loaded impact hammer and clamp for fracture of intimal occlusions by application of a sudden blow to the outside of the artery. Since the intima has become brittle as a result of occlusive structure, while the remaining layers of arterial tissue remain flexible, a sudden blow of proper strength will fracture the occlusive material without damaging the artery. The fractured material is then carried away from the site by the bloodstream and is disposed in normal cardiovascular processes. While this device can act on arteries of a broad range of diameters, it nonetheless requires access by the physician to the exterior of the artery by surgery.

U.S. Pat. No. 3,811,446 discloses a catheter with vibrating tip for insertion in the occlusive site by surgical access. This system also takes advantage of the fact that the exterior arterial layers are more elastic than the occlusive material. The tip of the catheter is a wire loop which is vibrated rapidly by a motor-drive outside the body. The repeated impact of the vibrated wire loop causes the exterior arterial layers to stretch and separate from the rigid, non-elastic occlusive material. The occlusive material is then removed from the artery and the artery is surgically closed. This device also has the disadvantage of requiring surgery to give access to the site of occlusion.

U.S. Pat. No. 4,273,128 discloses a balloon catheter combined with a knife tip for removal of occlusive material. The tip of the catheter is a flexible probe of minimum diameter, which is followed by the knife blades and then by the balloon. The knife blades are semi-circular and radiate outward from the central axis of the device. When the leading probe has reached the occlusion site, the device is pressed forward and the knife blades are rotated to drill through the central portion of the occlusion, thereby removing enough brittle material so that the balloon may be positioned within the occlusion and expand to dilate the site as described above. While this system offers the advantage of treatment by catheterization rather than the more traumatic surgery, it exposes the entire length of the artery, from insertion to occlusion, to the knife blades. Since an artery may normally follow a non-linear path, this entails some danger to the patient. Furthermore, since these blade are also of fixed diameter, blades of differing diameters are required to fit within arteries of different diameters.

Thus it can be seen that the need exists in the art for a method and apparatus for treatment of atherosclerotic conditions which does not involve the necessity of surgery, and which allows the physician to treat arteries of any diameter with one and the same apparatus. The new system should also avoid exposure of the arterial lumen to knife blades operated remotely.

SUMMARY OF THE INVENTION

The present invention comprises a novel balloon catheter and pulse generator system which removes occlusive material by exerting pulses of pressure from within the affected artery or vein. The balloon of the balloon catheter is guided to the affected site in a deflated state, and is then inflated by water or other fluid passed through a lumen defined within the catheter from a fluid supply source such as a syringe. When the balloon is in full contact with the occlusive material, the pulse generator creates pulses of pressure which are transmitted through the fluid in the lumen to the balloon. As each pressure pulse reaches the balloon, the balloon expands sharply and exerts stress on the occlusive material. Since the wall surrounding the occlusive material is elastic, it expands in response to the pressure pulse, while the occlusive material itself is more brittle. Therefore, the occlusive material retains its diameter, while cracking and separating from the exterior wall. The fractured occlusive material then is removed through normal cardiovascular processes.

It can be appreciated that the present invention avoids the necessity of major surgery by utilizing the well-known balloon catheter insertion procedure which is less traumatic to the patient. The balloon itself can be used to exert stress on occlusive material and arteries of any diameter without presenting the hazard of sharpened edges within or without the occlusive site. These and other objects and advantages of the present invention may be more readily appreciated when read in conjunction with the following description of the drawings and the detailed description of the preferred embodiment of the present invention.

BRIEF DESCRIPTION OF THE DRAWINGS

FIG. 1 is a perspective view of the inventive apparatus showing the balloon catheter and the pulse generator;

FIG. 2 is an isolated perspective view of the pulse motor housing of the pulse generator;

FIG. 3 is a cut-away view taken along line A—A' of FIG. 2;

FIG. 4 is an isolated cut-away view taken along line B—B' of FIG. 3; and

FIG. 5 is an isolated cut-away view of the balloon catheter of FIG. 1 placed in position within an artery for application of therapy.

DETAILED DESCRIPTION OF DRAWINGS

The best mode and preferred embodiment of the invention is illustrated in FIGS. 1-4. The inventive apparatus, generally indicated at 10, comprises a balloon catheter 20 and pulse generator 25 including pulse syringe 12 and pulse motor 30.

The balloon catheter 20 may be any conventionl well-known type defining a through-going lumen 22, a balloon 24 attached to the proximal end of lumen 22, and a supply syringe 26 attached to the distal end of lumen 22. The balloon 24 is collapsible to approximate the external diameter of catheter 20, and supply syringe 26 is adapted to force a fluid such as water through lumen 22 to inflate balloon 24 for purposes of therapy when balloon 24 is properly positioned within the arterial system of a patient.

Adjacent to supply syringe 26, balloon catheter 20 passes through T-joint 28 which includes valve 29. A pulse syringe 12 is also connected to T-joint 28, and includes piston 14, cylinder 16, fluid egress 18, and finger grips 27. Pulse syringe 12 is typically, though not necessarily, of much smaller fluid volume than supply syringe 26. Valve 29 may be used to connect or disconnect the fluid egress 18 of pulse syringe 12 to the fluid within lumen 22.

Pulse syringe 12 is held within syringe cradle 54 of pulse motor 30. As will be explained more fully below, pulse motor 30 depresses and releases piston 14 of pulse syringe 12 very rapidly, so as to produce low-volume high-pressure pulses of fluid within catheter 22. Pulse motor 30 is in turn driven by rotary motor 50, which may be of any standard well-known conventional type such as an electric motor, and will therefore not be described further herein.

Turning now to FIGS. 2-4, the pulse motor 30 comprises a housing 32 which may be divided along seam 33 into two equal symmetrical halves. The halves may be joined across seam 33 by back latch plate 56 and front latch plate 58. Front latch plate 58 also serves to restrain pulse syringe 12 within syringe cradle 54. Syringe grips 27 rest within grip slots 55, and the end of piston 14 rests extended into contact space 52 defined by housing 32.

Housing 32 encloses cam rotor 34 which is rotated by motor 50 in the direction illustrated by arrow 35. A slideway 38 is defined within housing 32 adjacent cam rotor 34. Slideway 38 contains coil spring 40 and ram 36. Ram 36 defines a ram slot 37 facing cam 34, which slot is engaged by cam rotor 34 to force ram 36 to slide along slideway 38 and compress spring 40. A front end portion 39 of ram 36 extends through contact bore 44 to the contact space 52, and is coupled to contact head 42 which faces piston 14. Contact head 42 is advantageously larger than the diameter of bore 44 and the contact surface of piston 14.

At the opposite end of slideway 38 from bore 44, housing 32 defines a bore 48. A force adjustment screw 46 extends from the exterior plate 56 through bore 48 to connect to force adjustment plate 47. Force adjustment plate 47 is substantially as wide as slideway 38 and contacts spring 40. The force exerted by spring 40 on ram 36 is proportional to the length of spring 40 along slideway 38, and adjustment of screw 46 will move plate 47 backward or forward along slideway 38 to increase or decrease the minimum length of spring 40 when compressed by action of cam rotor 34 as described below.

In operation of the present inventive apparatus, the patient is made ready for insertion of the balloon catheter 20 and the valve 29 is closed to disconnect pulse syringe 14 from the catheter 22. Any standard surgical procedure may be used to insert the balloon catheter 20 with the balloon 24 deflated in the arterial system of the patient, as well as to place the deflated balloon 24 at the atherosclerotic site. In this regard, it may be advantageous to fill lumen 22 with a radio-opaque fluid, or to place metallic bands at specific intervals along catheter 20, to enable radiographic tracking of the balloon and catheter.

When the balloon 24 is in place, supply syringe 26 is utilized to inflate balloon 24 until contact with the walls of the artery 100 is made and some pressure is exerted thereon, as shown in FIG. 5.

When balloon 24 is properly in place and inflated, motor 50 may be started and valve 29 opened to transmit pressure pulses from pulse syringe 12 through the fluid of balloon catheter 20. As cam rotor 34 rotates, a cam point will engage slot 37 and force ram 36 back along slideway 38, thereby compressing spring 40 between ram 36 and plate 47. When the cam rotor 34 rotates to the position shown in FIG. 3, the cam point lifts out of slot 37, thereby removing the obstacle to expansion of spring 40. The sudden expansion of spring 40 drives ram 36 forward along slideway 38, so that contact head 42 contacts piston 14 and forces a sudden pulse of fluid from syringe 12 through balloon catheter 20. Thereafter, another point of cam rotor 34 re-engages slot 37, and ram 36 is once again withdrawn back through slideway 38 to re-compress spring 40. This provides room for piston 14 to withdraw from cylinder 16 and allows the fluid within balloon catheter 20 to expand back into cylinder 16, thereby resuming its normal pressure.

The frequency of these pressure pulses can be controlled by regulating the speed of motor 50. The pressure exerted in each pulse can be regulated by adjustment of screw 46 to alter the compressed length of spring 40.

Since the balloon 24 is inflated to contact the atherosclerotic site prior to transmission of pressure pulses, as each pulse arrives the balloon is fully in contact with the arterial wall and therefore exerts pressure on the wall rather than expanding to meet the wall in response to each pressure pulse. Because the intima produced by the diseased condition is very brittle as compared to the normal arterial wall, each pressure pulse exerts stress on the brittle material while forcing the exterior elastic wall to expand away therefrom. Repeated pulses result in shattering of the brittle intima, and the fragments thereof separate from the expanded wall and are carried away by normal cardiovascular processes.

The balloon can be inflated to any diameter, in order to accommodate any diameter passageway from a highly occluded small artery to a space several time wider than catheter 20. The system requires no surgical access to the exterior of the site, nor does it expose the interior to potentially traumatic blades. At the completion of therapy, the valve 29 is again closed and fluid is withdrawn into syringe 26, thereby deflating the balloon to the diameter of catheter 20. The catheter is then withdrawn from the body of the patient.

For purposes of accurate inflation of the balloon to a predetermined diameter, it is advantageous to place calibration markings on the supply syringe, either for fluid volume or for balloon diameter. The rotary motor may be a stepping electric motor, to provide single pulse therapy, or a variable speed electric motor, to provide pulse frequency control.

It should be understood that the embodiment disclosed hereinabove is not meant to limit the invention in any manner. On the contrary, it is intended to cover all modifications, alternatives and equivalents as may be included within the spirit and scope of the invention as defined by the following claims.

What is claimed is:

1. An apparatus for removal of atherosclerotic occlusions comprising, in combination: balloon catheter means, said balloon catheter means comprising flexible catheter means, said catheter means defining a through-going lumen, a proximal end, and a distal end, fluid supply means adapted to fill said lumen of said catheter means with fluid, balloon means operatively connected to said proximal end of said catheter means and communicating with said lumen, pulse generator means comprising pulse motor means, cylinder means, and piston means moveably mounted in said cylinder means, said pulse motor means being adapted to repeatedly impact and release said piston means to force reciprocal movement of said piston means through said cylinder means, and valve means attached to said fluid supply means, said cylinder means and said lumen, and adapted to operatively connect alternatively said fluid supply means or said cylinder means to said lumen.

2. The apparatus as claimed in claim 1, wherein said fluid supply means comprises supply syringe means.

3. The apparatus as claimed in claim 2, wherein said supply syringe is calibrated to indicate the volume of said fluid injected from said supply syringe through said lumen means.

4. The apparatus as claimed in claim 2, wherein said supply syringe is calibrated to indicate the diameter of said balloon means inflated by injection of said fluid from said supply syringe through said lumen means.

5. The apparatus as claimed in claim 1, wherein said pulse motor means comprises a cam rotor, a rotary motor adapted to rotate said cam rotor, a ram aligned with said piston means and adapted to be alternately driven away from said piston means and then released by said cam rotor, and a spring adjacent said ram and adapted to be compressed by said ram when driven by said cam rotor and to expand when said ram is released by said cam rotor to drive said ram forward to contact said piston means and inject said pulse of said fluid into said lumen.

6. The apparatus as claimed in claim 5, wherein said rotary motor is a variable speed electric motor.

7. The apparatus as claimed in claim 5, wherein said rotary motor is a stepping electric motor.

8. An apparatus for treatment of atherosclerotic occlusions comprising, in combination: a catheter, said catheter defining a proximal end, a distal end, and a through-going lumen, a supply syringe, said supply syringe being connected to said distal end and being adapted to supply fluid through said lumen, a balloon mounted to said proximal end of said catheter, said balloon being adapted to be inflated by fluid from said supply syringe through said lumen; and a pulse generator, said pulse generator including a pulse syringe, said pulse syringe being coupled to said catheter adjacent said distal end and being adapted to supply pressure pulses in fluid contained in said lumen, and a pulse motor adapted to create pressure pulses in said pulse syringe, said pulse motor including a ram aligned with said pulse syringe and adapted to strike said pulse syringe, a spring adjacent said ram opposite said pulse syringe, a cam rotor positioned adjacent said ram adapted to alternately drive said ram against said spring to compress said spring and then release said ram, and a rotary motor adapted to rotate said cam rotor.

9. The apparatus as claimed in claim 8, wherein said fluid is radio-opaque.

10. The apparatus as claimed in claim 8, wherein said catheter is banded with metal at specific intervals.

11. The apparatus as claimed in claim 8, wherein said fluid is water.

* * * * *